US006730313B2

(12) United States Patent
Helmus et al.

(10) Patent No.: US 6,730,313 B2
(45) Date of Patent: May 4, 2004

(54) DELIVERY SYSTEMS FOR PERIADVENTITIAL DELIVERY FOR TREATMENT OF RESTENOSIS AND ANASTOMOTIC INTIMAL HYPERPLASIA

(75) Inventors: Michael N. Helmus, Worcester, MA (US); Crystal M. Cunanan, Mission Viejo, CA (US); Patrice Tremble, Santa Rosa, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/771,480

(22) Filed: Jan. 25, 2001

(65) Prior Publication Data

US 2002/0026236 A1 Feb. 28, 2002

Related U.S. Application Data

(60) Provisional application No. 60/178,087, filed on Jan. 25, 2000.

(51) Int. Cl.⁷ .............................. A61F 2/02; A61K 9/50
(52) U.S. Cl. ..................... 424/423; 424/501; 424/502
(58) Field of Search ......................... 424/423, 501, 424/502

(56) References Cited

U.S. PATENT DOCUMENTS

| | | | |
|---|---|---|---|
| 4,393,041 A | 7/1983 | Brown et al. |
| 4,532,134 A | 7/1985 | Malette et al. |
| 4,909,251 A | 3/1990 | Seelich |
| 4,937,324 A | 6/1990 | Fujikawa et al. |
| 5,137,734 A | 8/1992 | Spiegelman et al. |
| 5,252,213 A | 10/1993 | Ahmad et al. |
| 5,270,047 A | 12/1993 | Kauffman et al. |
| 5,398,691 A | 3/1995 | Martin et al. |
| 5,410,016 A | 4/1995 | Hubbell et al. |
| 5,443,827 A | 8/1995 | Haber et al. |
| 5,455,039 A | 10/1995 | Edelman et al. |
| 5,470,957 A | 11/1995 | Reed |
| 5,498,531 A | 3/1996 | Jarrell |
| 5,522,840 A | 6/1996 | Krajicke |
| 5,527,532 A | 6/1996 | Edelman et al. |
| 5,540,912 A | 7/1996 | Roorda et al. |
| 5,567,435 A | 10/1996 | Hubbell et al. |
| 5,607,694 A | 3/1997 | Marx |
| 5,616,469 A | 4/1997 | Brawer |
| 5,622,843 A | 4/1997 | Day et al. |
| 5,626,863 A | 5/1997 | Hubbell et al. |
| 5,631,011 A | 5/1997 | Wadstrom |
| 5,631,019 A | 5/1997 | Marx |
| 5,632,986 A | 5/1997 | Tait et al. |
| 5,634,895 A | 6/1997 | Igo et al. |
| 5,650,447 A | 7/1997 | Keefer et al. |
| 5,651,982 A | 7/1997 | Marx |
| 5,653,744 A | 8/1997 | Khouri |
| 5,658,882 A | 8/1997 | Celeste et al. |
| 5,688,694 A | 11/1997 | Brawer |
| 5,713,891 A | 2/1998 | Poppas |
| 5,752,974 A | 5/1998 | Rhee et al. |
| 5,766,584 A | 6/1998 | Edelman et al. |
| 5,780,272 A | 7/1998 | Jarrell |
| 5,814,066 A | 9/1998 | Spotnitz |
| 5,824,049 A | 10/1998 | Ragheb et al. |
| 5,834,274 A | 11/1998 | Hubbell et al. |
| 5,851,521 A | 12/1998 | Branellec et al. |
| 5,879,713 A * | 3/1999 | Roth et al. |
| 6,544,541 B1 * | 4/2003 | Zahradka |

FOREIGN PATENT DOCUMENTS

| | | |
|---|---|---|
| EP | 0481160 A1 | 4/1991 |
| EP | 0534178 A2 | 9/1992 |
| EP | 0592242 A1 | 10/1993 |
| EP | 0970711 A2 | 1/2000 |
| WO | WO 85/03640 | 8/1985 |
| WO | WO 92/09301 | 6/1992 |
| WO | WO 92/22312 | 12/1992 |
| WO | WO 93/19805 | 10/1993 |
| WO | WO 94/19016 | 9/1994 |
| WO | WO 94/20133 | 9/1994 |
| WO | WO 94/22503 | 10/1994 |
| WO | WO 94/28949 | 12/1994 |
| WO | WO 95/22316 | 8/1995 |
| WO | WO 95/29686 | 11/1995 |
| WO | WO96/40174 | 12/1996 |
| WO | WO98/51369 | 11/1998 |
| WO | WO99/21908 | 5/1999 |
| WO | WO00/09088 | 2/2000 |

* cited by examiner

Primary Examiner—Carlos A. Azpuru
(74) Attorney, Agent, or Firm—John Christopher James; Rajiv Yadav; Edwards Lifesciences Corp.

(57) ABSTRACT

The invention provides methods for treating injuries to one or more internal structures of a subject by administering a drug delivery vehicle to an external surface of the injured structure. The drug delivery vehicle substantially adheres to the site of administration and provides for the release of a bioactive agent that reduces or prevents further injury to the internal structure by disease processes, such as hyperplasia.

61 Claims, No Drawings

DELIVERY SYSTEMS FOR PERIADVENTITIAL DELIVERY FOR TREATMENT OF RESTENOSIS AND ANASTOMOTIC INTIMAL HYPERPLASIA

CROSS-REFERENCE TO RELATED APPLICATIONS

The present application claims priority to U.S. Patent Application Ser. No. 60/178,087, filed on Jan. 25, 2000, the disclosure of which is incorporated herein in its entirety for all purposes.

BACKGROUND OF THE INVENTION

The hollow or tubular geometry of organs has functional significance, such as in the facilitation of fluid or gas transport (e.g., blood, urine, lymph and respiratory gases) or cellular containment (e.g., sperm, ova). Disease processes may affect organs or their components by encroaching upon, obstructing or otherwise reducing the cross-sectional area of the hollow or tubular elements. The ability of the organ to properly function can be severely compromised. An illustrative example of this phenomenon can be seen by reference to coronary vasculature.

Coronary arteries are often subject to attack by disease processes, most commonly by atherosclerosis. In atherosclerosis, the coronary vessels become lined with lesions known as plaques. The development of plaques leads to a decrease in vessel cross-sectional area and a concomitant compromise in blood flow through the vessel. The reduction in blood flow to the coronary muscle can result in clinical angina, unstable angina or myocardial infarction and death.

Historically, the treatment of advanced atherosclerotic vascular disease involved cardio-thoracic surgery in the form of coronary artery bypass grafting (CABG). Such artery bypass grafting is not limited to use with the coronary muscle, but is also used to treat heart and renal failure, arterial aneurysms, and other conditions that require general vascular bypass to restore blood flow to areas of ischemia. Another commonly used method for restoring blood flow to occluded vasculature is percutaneous coronary angioplasty. Angioplasty is a routinely-utilized surgical procedure for the treatment of diseases, such as atherosclerosis and medial arteriosclerosis. Both CABG and angioplasty normally involve injury to a portion of an artery or vein. In many cases the injury is followed by implantation of a donor or synthetic vascular graft, stent, or other implant in order to replace or repair the injured vascular or heart portion.

The treatment of intravascular diseases by angioplasty is relatively non-invasive. Techniques, such as percutaneous transluminal angioplasty (PTA) and percutaneous transluminal coronary angioplasty (PTCA) typically involve use of a guide wire. A typical balloon catheter has an elongate shaft with a balloon attached to its distal end and a manifold attached to the proximal end. In use, the balloon catheter is advanced over the guide wire such that the balloon is positioned adjacent a restriction in a diseased vessel. The balloon is then inflated and the restriction in the vessel is dilated.

Vascular restrictions that have been dilated do not always remain open. In up to 50% of the cases, a new restriction in the lumen of the vascular structure appears over a period of months. The newly formed restriction, or "restenosis," arises due to the onset and maintenance of intimal hyperplasia at the site of insult. Restenosis and intimal hyperplasia following a procedure on a vascular structure is discussed in the following publications, see, for example Khanolkar, *Indian Heart J.* 48:281–282 (1996); Ghannem et al., *Ann. Cardiol. Angeiol.* 45:287–290 (1996); Macander et al., *Cathet. Cardiovasc. Diagn.* 32:125–131; Strauss et al., *J. Am. Coll. Cardiol.* 20:1465–1473 (1992); Bowerman et al., *Cathet. Cardiovasc. Diagn.* 24:248–251 (1991); Moris et al., *Am. Heart. J.* 131:834–836 (1996); Schomig et al., *J. Am. Coll. Cardiol.* 23:1053–1060 (1994); Gordon et al., *J. Am. Coll. Cardiol.* 21:1166–1174; and Baim et al., *Am. J. Cardiol.* 71:364–366 (1993).

Intimal hyperplasia also arises in conjunction with vascular reconstructive surgery. Vascular reconstructive surgery involves removing or reinforcing an area of diseased vasculature. Following removal of the diseased portion of the vessel, a prosthetic device, such as an endovascular stent graft or prosthetic graft is implanted at the site of removal. The graft is typically a segment of autologous or heterologous vasculature or, alternatively, it is a synthetic device fabricated from a polymeric material. Stent grafts are generally fabricated from metals, polymers and combinations of these materials. Similar to the situation with angioplasty, intimal hyperplasia also causes failure of implanted prosthetics in vascular reconstructive surgery. Thus, a method to reduce the failure rate for angioplasty and vascular reconstructive surgery by preventing or reducing intimal hyperplasia is an avidly sought goal.

Intimal hyperplasia is the result of a complex series of biological processes initiated by vascular injury followed by platelet aggregation and thrombus formation with a final pathway of smooth muscle cell migration and proliferation and extracellular matrix deposition. Platelets adhere and aggregate at the site of injury and release biologically active substances, the most important of which are platelet-derived growth factors (Scharf et al., *Blut* 55:1131–1144 (1987)). It has been postulated that intimal hyperplasia production is driven by two principal mechanisms; platelet activation with the release of platelet-derived growth factors, and activation of the coagulation cascade with thrombus formation, which also results in the release of biologically active substances, which can contribute to smooth muscle cell proliferation (Chervu et al., *Surg. Gynecol. Obstet.* 171:433–447, 1990)).

Attempts to prevent the onset, or to mitigate the effects, of intimal hyperplasia have included, for example, drug therapy with antihyperplastic agents, such as antiplatelet agents (e.g. aspirin, arachidonic acid, prostacyclin), antibodies to platelet-derived growth factors, and antithrombotic agents (e.g. heparin, low molecular weight heparins) (see, Ragosta et al. *Circulation* 89: 11262–127 (1994)). Clinical trials using antihyperplastic agents, however, have shown little effect on the rate of restenosis (Schwartz, et al., *N. Engl. J. Med.* 318:1714–1719, (1988); Meier, *Eur. Heart J.* 10 (suppl G):64–68 (1989)). In both angioplasty and vascular reconstructive surgery, drug infusion near the site of stenosis has been proposed as a means to inhibit restenosis. For example, U.S. Pat. No. 5,558,642 to Schweich et al. describes drug delivery devices and methods for delivering pharmacological agents to vessel walls in conjunction with angioplasty.

In addition to simply administering a bioactive agent to a patient to prevent restenosis, a number of more sophisticated methods have been investigated. For example, to address the restenosis problem in vascular reconstruction, it has been proposed to provide stents which are seeded with endothelial cells (Dichek et al., *Circulation* 80:1347–1353(1989). Both autologous and heterologous cells have been used (see, for example, Williams, U.S. Pat. No. 5,131,907, which issued on Jul. 21, 1992; and Herring, *Surgery* 84:498–504 (1978)).

Methods of providing therapeutic substances to the vascular wall by means of drug-coated stents have also been proposed. For example, methotrexate and heparin have been incorporated into a cellulose ester stent coating. The drug treated stent, however, failed to show a reduction in restenosis when implanted in porcine coronary arteries (Cox et al., Circulation 84: II71 (1991)). Implanted stents have also been used to carry thrombolytic agents. For example, U.S. Pat. No. 5,163,952 to Froix discloses a thermal memoried expanding plastic stent device, which can be formulated to carry a medicinal agent by utilizing the material of the stent itself as an inert polymeric drug carrier. Pinchuk, in U.S. Pat. No. 5,092,877, discloses a stent of a polymeric material which can be employed with a coating that provides for the delivery of drugs. Ding et al., U.S. Pat. No. 5,837,313 disclose a method of coating an implantable open lattice metallic stent prosthesis with a drug releasing coating.

Other patents which are directed to devices of the class utilizing biodegradable or biosorbable polymers include, for example, Tang et al., U.S. Pat. No. 4,916,193, and MacGregor, U.S. Pat. No. 4,994,071. Sahatjian in U.S. Pat. No. 5,304,121, discloses a coating applied to a stent consisting of a hydrogel polymer and a preselected drug; possible drugs include cell growth inhibitors and heparin. Drugs have also been delivered to the interior of vascular structures by means of a polyurethane coating on a stent. The coating was swelled and a biologically active compound was incorporated within the interstices of the polymer (Lambert, U.S. Pat. No. 5,900,246, which issued May 4, 1999).

The use of stents, as described above, is accompanied by certain disadvantages. For example, in many cases, it is desirable to precondition the structure with anti-hyperplastic agents prior to their undergoing a surgical procedure. As placing a stent requires disrupting the border of the structure in which the stent is to be placed, it is not possible to use a drug-coated stent to precondition a tissue. Moreover, when the drug has diffused out of a drug-loaded stent, it is not possible to administer additional doses of the drug if necessary without replacing the stent and subjecting the repaired structure to additional trauma.

In another method, Edelman et al. have utilized a solid matrix, seeded with vascular endothelial cells (U.S. Pat. No. 5,766,584). The delivery vehicle consists of a three-dimensional matrix onto which endothelial cells are seeded. When the seeded endothelial cells have reached the desired density within the matrix, a vascular structure that has undergone an invasive procedure is wrapped with the seeded matrix. The endothelial cells within the matrix secrete products that diffuse into the surrounding tissue without migrating to the endothelial cell lining of the blood vessel. A procedure that relies on wrapping an injured vascular structure with a delivery matrix is less than ideal. For example, as it is generally desirable for the surgical procedure to be minimally invasive and for the surgical field to be of the smallest possible size, there is a stringent practical limitation the size of the area that can be wrapped and the thickness of the matrix wrapped around the circumference of a vascular structure. Moreover, the endothelial cell-based approaches have not been broadly accepted, because they require that endothelial cell cultures from a patient be established and that the cells be seeded at high densities within the polymeric matrix.

In another method, a modulator of cell or tissue growth is delivered to an extraluminal site adjacent to the point of vascular injury by means of an implanted infusion pump or biodegradable vehicle (Edelman, et al., U.S. Pat. No. 5,527,532). In one embodiment of the Edelman invention, the biodegradable vehicle is implanted in the adventitia at a site adjacent to the site of injury. The modulator is delivered to the adventitia and from the aventitia to exterior surface of the vascular wall.

Neither of the methods disclosed by Edelman et al. address coating directly the exterior surface of a vascular or other tubular structure with a flowable drug delivery matrix into which a therapeutic agent has been dispersed. Moreover, Edelman et al. does not disclose the use of a delivery vehicle that is substantially adherent to the exterior surface of an internal structure of a patient.

A method of preventing or retarding intimal hyperplasia by delivering a therapeutic agent to the site of injury using a drug delivery vehicle implanted on the exterior surface of the injured structure would represent a substantial advance in the art. Moreover, it would be desirable if the method was flexible enough to allow the agents to be applied prior to the surgery and to be reapplied following the surgery. Quite surprisingly, the present invention provides such a method.

SUMMARY OF THE INVENTION

It has now been discovered that antihyperplastic and other useful agents can be delivered to internal organs and other tissues by a periadventitial route by layering a bioadhesive material containing a desired agent on the exterior surface of the organ or other tissue. Although the methods described herein are of general applicability, the present invention particularly concerns a method for inhibiting intimal hyperplasia induced by arterial interventions by administering, periadventitially at the site of the vascular injury, a bioactive compound that inhibits intimal hyperplasia.

Thus, in a first aspect, the present invention provides a method of preventing or reducing intimal hyperplasia at a site of insult to an internal structure in a subject. The method comprises, contacting an exterior surface of the internal structure with a drug delivery vehicle. The drug delivery vehicle is generally deposited as a substantially flowable liquid or semi-liquid material onto the exterior surface of the internal structure to which it will, preferably, substantially adhere. The drug delivery vehicle comprises at least one intimal hyperplasia-preventing agent that is released from the drug delivery vehicle in a time dependent manner and in an amount effective to prevent or reduce intimal hyperplasia.

In a second aspect, the present invention provides a method of preventing or reducing intimal hyperplasia at a site of insult to a vascular structure in a subject. The insult is a member selected from the group consisting of angioplasty, vascular reconstructive surgery and combinations thereof. The method comprises, contacting an exterior surface of the internal structure with a drug delivery vehicle. The drug delivery vehicle is generally deposited as a substantially flowable liquid or semi-liquid material onto the exterior surface of the internal structure to which it will, preferably, substantially adhere. The drug delivery vehicle comprises at least one intimal hyperplasia-preventing agent that is released from the drug delivery vehicle in a time dependent manner and in an amount effective to prevent or reduce intimal hyperplasia.

In a third aspect, the present invention provides a method of treating a disease state of an internal structure in a subject. The method comprises surgically treating the disease state. The surgical treatment creates a surgical site that is treated by contacting an exterior surface of the internal structure with a drug delivery vehicle. The region of the external surface contacted with the drug delivery vehicle is contiguous with the surgical site. The drug delivery vehicle is deposited on the external surface as a substantially flowable liquid or semi-liquid material. The drug delivery vehicle is, preferably, substantially adherent to the external surface of the internal structure. The drug delivery vehicle comprises one or more intimal hyperplasia-preventing agent that is released in a time dependent manner and in an amount effective to prevent or reduce said intimal hyperplasia.

Other objects and advantages of the present invention will be apparent from the detailed description that follows

DETAILED DESCRIPTION OF THE INVENTION AND THE PREFERRED EMBODIMENTS

A. Definitions

As used herein, the term "contiguous," refers to a location that is coextensive with the site of a surgical or other insult. When the insult is angioplasty, an area "contiguous" with the site of insult will generally be on an area of the external surface of the vascular structure.

"Internal structure," as used herein refers to structures such as vascular structures (e.g., vessels, heart), organs (e.g., stomach, liver, intestines) and the like. Preferred internal structures include those having a substantially circular cross-section, such as the organs of the digestive system and reproductive and urinary systems.

"Time dependent manner," as used herein refers to the release of a drug from a drug delivery vehicle with zero-order or higher order kinetics.

"Flowable," as used herein refers to the ability to extrude the vehicle through an opening in a delivery device, such as a needle, catheter, atomizer and the like.

B. Introduction

Intimal hyperplasia (also referred to as neointimal hyperplasia) refers to a proliferative response to a vascular injury consisting of smooth muscle cells (SMCs) which form an intimal lesion on the luminal surface around the inner circumference of a blood vessel (intima) following a vascular intervention such as, e.g., angioplasty or endarterectomy. The hyperplastic growth gradually encroaching into the lumen of the blood vessel is the leading cause of restenosis. Hyperplasia occurs gradually over a period of days to several weeks following the arterial intervention, as distinguished from a thrombus, such as may occur in the circulating blood immediately at the time of intervention.

It is estimated that well over one million arterial interventions are performed each year in the United States for the treatment of occlusive arterial disease (see, Califf et al., *J. Am. Coll. Cardiol.* 17:2B–13B (1991)). The early results of these procedures are generally excellent. Within about six months to five years, however, over 50% of the treated arteries develop restenosis and require reintervention. Most develop restenosis within the first year. Consequently, in many clinics, up to 50% of the case load consists of secondary procedures as opposed to first interventions.

Thus, in a first aspect, the present invention provides a method of preventing or reducing intimal hyperplasia at a site of insult to an internal structure in a subject. The method comprises, contacting an exterior surface of the internal structure with a drug delivery vehicle. The drug delivery vehicle is generally deposited as a substantially flowable liquid or semi-liquid material onto the exterior surface of the internal structure to which it will, preferably, substantially adhere. The drug delivery vehicle comprises at least one intimal hyperplasia-preventing agent that is released from the drug delivery vehicle in a time dependent manner and in an amount effective to prevent or reduce intimal hyperplasia.

In another aspect, the present invention provides a method of treating a disease state of an internal structure in a subject. The method comprises surgically treating the disease state. The surgical treatment creates a surgical site that is treated by contacting an exterior surface of the internal structure with a drug delivery vehicle. The region of the external surface contacted with the drug delivery vehicle is contiguous with the surgical site. The drug delivery vehicle is deposited onto the external surface of the of the internal structure as a flowable liquid or semi-liquid material. The deposited drug-delivery matrix will, preferably, substantially adhere to the external surface of the internal structure. The drug delivery vehicle comprises one or more intimal hyperplasia preventing agent that is released in a time dependent manner and in an amount effective to prevent or reduce said intimal hyperplasia.

The method of the present invention can be practiced on any internal structure of any mammal. In a presently preferred embodiment, the internal structure is a structure having a substantially circular cross-section. Exemplary structures having substantially circular cross-sections include, but are not limited to, vascular system components, intestinal system components, urinary system components, reproductive system components and combinations thereof. In a presently preferred embodiment, the internal structure is a vascular structure.

The method of the invention can be practiced in conjunction with substantially to an internal structure, including, for example, a disease, a degenerative condition, an injury or trauma, and a surgical insult.

In a preferred embodiment, the insult is a surgical insult. In a further preferred embodiment, the surgical insult derives from a technique, such as angioplasty, vascular reconstructive surgery, heart valve replacement, heart transplantation and combinations thereof. In a presently preferred embodiment, the method is practiced in conjunction with vascular reconstructive surgery, angioplasty and combinations thereof.

In another preferred embodiment, the surgical injury comprises placing a prosthesis at the site of insult to the internal structure. Preferred prostheses include, but are not limited to stents, grafts, valves or a combination thereof. When a prosthetic device is implanted, the method of the invention is preferably practiced by contacting the prosthetic, the site of insult and combinations thereof with the drug delivery vehicle. In a preferred embodiment, the drug delivery vehicle is layered on the exterior surface of the internal structure so that the delivery vehicle encompasses both the prosthesis and the site of insult.

In another preferred embodiment, the insult is, for example, CABG and the site of insult comprises an anastomosis. In this embodiment, the exterior surface of the vascular structure contacted with the drug delivery vehicle comprises the anastomosis.

The method of the invention can be practiced at substantially any time relative to the onset of the insult. For example, in a preferred embodiment, the insult is a surgical insult and the method is practiced on an internal structure prior to its undergoing the surgical insult as a form of presurgical conditioning. In this embodiment, the method can be practiced again during and/or following the surgical insult. In another preferred embodiment, the method is practiced during surgery and is optionally practiced one or more times following surgery. Other appropriate times relative to insult for practicing the method of the invention will be apparent to those of skill in the art.

C. Bioactive Agents

Any bioactive agent that is capable of retarding or arresting the formation of intimal hyperplasia is appropriate for incorporation into the coating of the invention. For reasons of clarity, the discussion that follows is focused on vascular reconstructive surgery involving implanting a vascular graft. Those of skill will readily appreciate that the discussion is generally applicable to other forms of vascular reconstructive surgery, angioplasty and preventing the formation of post-surgical adhesions in other organs and/or internal structures.

Intimal hyperplasia is caused by a cascade of events in response to vascular damage. As part of the inflammatory and reparative response to vascular damage, such as that resulting from vascular surgeries, inflammatory cells (e.g., monocytes, macrophages, and activated polymorphonuclear leukocytes and lymphocytes) often form inflammatory lesions in the blood vessel wall. Lesion formation activates cells in the intimal and medial cellular layers of the blood vessel or heart. The cellular activation may include the migration of cells to the innermost cellular layers, known as the intima. Such migrations pose a problem for the long-term success of vascular grafts because endothelial cells release smooth muscle cell growth factors (e.g., platelet-derived growth factor, interleukin-1, tumor necrosis factor, transforming growth factor-beta, and basic fibroblast growth factor), that cause these newly-migrated smooth muscle cells to proliferate. Additionally, thrombin has been demonstrated to promote smooth muscle cell proliferation both by acting as a growth factor itself and by enhancing the release of several other growth factors produced by platelets and endothelial cells (Wu et al., Annu. Rev. Med. 47:315–31 (1996)). Smooth muscle cell proliferation causes irregular and uncontrolled growth of the intima into the lumen of the blood vessel or heart, which constricts and often closes the vascular passage. Often, irregular calcium deposits in the media or lipid deposits in the intima accompany smooth muscle cell growths, such lipid deposits normally existing in the form of cholesterol and cholesteryl esters that are accumulated within macrophages, T lymphocytes, and smooth muscle cells. These calcium and lipid deposits cause arteriosclerotic hardening of the arteries and veins and eventual vascular failure. These arteriosclerotic lesions caused by vascular grafting can also be removed by additional reconstructive vascular surgery, but the failure rate of this approach due to restenosis has been observed to be between thirty and fifty percent.

Any bioactive agent that can interrupt or retard one or more of the elements of the above-described hyperplastic cascade is useful in practicing the present invention. Example of useful bioactive agents include, but are not limited to, antithrombotics, antiinflammatories, corticosteroids, antimicrotubule agents, antisense oligonucleotides, antineoplastics, antioxidants, antiplatelets, calcium channel blockers, converting enzyme inhibitors, cytokine inhibitors, growth factors, growth factor inhibitors, growth factor sequestering agents, immunosuppressives, tissue factor inhibitor, smooth muscle inhibitors, organoselenium compounds, retinoic acid, retinoid compounds, sulfated proteoglycans, superoxide dismutase mimics, NO, NO precursors and combinations thereof.

Certain biologically active agents falling within the above-recited classes are presently preferred. For example, when one or more of the bioactive agents is an antithrombotic agent, it is preferably selected from heparin, hirudin or a combination thereof. When one or more of the bioactive agents is a corticosteriod, it is preferably selected from dexamethasone, a dexamethosone derivative or a combination thereof. When one or more of the bioactive agents is an antimicrotubule agent, it is preferably selected from taxane, a derivative of taxane or a combination thereof. When one or more of the bioactive agents is an antiplatelet agent, the agent is preferably an inhibitor of collagen synthesis, such as halofuginore, derivatives of halofuginore, proteins (e.g., $GpII_bIII_a$, ReoPro™) or a combination thereof.

Pharmaceutically acceptable salts of the biologically active agents are also of use in the present invention. Exemplary salts include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like.

Other agents that are useful in conjunction with the present invention will be readily apparent to those of skill in the art.

D. Incorporation of Bioactive Agents

The bioactive agents useful in practicing the present invention can be incorporated into drug delivery vehicles ("coatings") useful in practicing the methods of the invention using one or more of the many art-recognized techniques for immobilizing, or adhering, drug molecules to other molecules and surfaces. These methods include, but are not limited to, covalent attachment to the coating of the drug or a derivative of the drug bearing a "handle" allowing it to react with a component of the delivery vehicle having a complementary reactivity. Moreover, the bioactive agent can be incorporated into the vehicle using a non-covalent interaction, such as an electrostatic or an ionic attraction between a charged drug and a component of the coating bearing a complementary charge. The bioactive agents can also be admixed, and not otherwise interact with, the components of the delivery vehicle. The coatings can also be fabricated to incorporate the drugs into reservoirs located in the coating. The reservoirs can have a variety of shapes, sizes and they can be produced by an array of methods. For example, the reservoir can be a monolithic structure located in one or more components of the coating. Alternatively, the reservoir can be made up of numerous small microcapsules that are, for example, embedded in the material from which the coating is fabricated. Furthermore, the reservoir can be a coating that includes the bioactive agent diffused throughout, or within a portion, of the coating's three-dimensional structure. The reservoirs can be porous structures that allow the drug to be slowly released from its encapsulation, or the reservoir can include a material that bioerodes following implantation and allows the drug to be released in a controlled fashion.

1. Covalently Attached Bioactive Materials

In a preferred embodiment, the biologically active material is covalently bonded to a reactive group located on one or more components of the coating. The art is replete with methods for preparing derivatized, polymerizable monomers, attaching bioactive materials onto polymeric surfaces and derivatizing bioactive materials and polymers to allow for this attachment (see, for example, Hermanson, BIOCONJUGATE TECHNIQUES, Academic Press, 1996, and references therein). Common approaches include the use of coupling agents such as glutaraldehyde, cyanogen bromide, p-benzoquinone, succinic anhydrides, carbodiimides, diisocyanates, ethyl chloroformate, dipyridyl disulfide, epichlorohydrin, azides, among others, which serve as attachment vehicles for coupling reactive groups of biologically active molecules to reactive groups on a monomer or a polymer.

A polymer can be functionalized with reactive groups by, for example, including a moiety bearing a reactive group as an additive to a blend during manufacture of the polymer or polymer precursor. The additive is dispersed throughout the polymer matrix, but does not form an integral part of the polymeric backbone. In this embodiment, the surface of the polymeric material is altered or manipulated by the choice of additive or modifier characteristics. The reactive groups of the additive are used to bind one or more bioactive agents to the polymer.

A useful method of preparing surface-functionalized polymeric materials by this method is set forth in, for example, Caldwell, U.S. Pat. No. 5,874,164, issued Feb. 23, 1999. In the Caldwell method, additives or modifiers are combined with the polymeric material during its manufacture. These additives or modifiers include compounds that have reactive sites, compounds that facilitate the controlled release of agents from the polymeric material into the surrounding environment, catalysts, compounds that promote adhesion between the bioactive materials and the polymeric material and compounds that alter the surface chemistry of the polymeric material.

In another embodiment, polymerizable monomers bearing reactive groups are incorporated in the polymerization mixture. The functionalized monomers form part of the polymeric backbone and, preferably, present their reactive groups on the surface of the polymer.

Reactive groups contemplated in the practice of the present invention include functional groups, such as hydroxyl, carboxyl, carboxylic acid, amine groups, and the like, that promote physical and/or chemical interaction with the bioactive material. The particular compound employed as the modifier will depend on the chemical functionality of the biologically active agent and can readily be deduced by one of skill in the art. In the present embodiment, the reactive site binds a bioactive agent by covalent means. It will, however, be apparent to those of skill in the art that these reactive groups can also be used to adhere bioactive agents to the polymer by hydrophobic/hydrophilic, ionic and other non-covalent mechanisms.

In addition to manipulating the composition and structure of the polymer during manufacture, a preferred polymer can also be modified using a surface derivitization technique. There are a number of surface-derivatization techniques appropriate for use in fabricating the delivery vehicles of the present invention (e.g., grafting techniques). These techniques for creating functionalized polymeric surfaces are well known to those skilled in the art. For example, techniques based on ceric ion initiation, ozone exposure, corona discharge, UV irradiation and ionizing radiation ($^{60}$Co, X-rays, high energy electrons, plasma gas discharge) are known and can be used in the practice of the present invention.

Substantially any reactive group that can be reacted with a complementary component on a biologically active material can be incorporated into a polymer and used to covalently attach the biologically active material to the coating of use in the invention. In a preferred embodiment, the reactive group is selected from amine-containing groups, hydroxyl groups, carboxyl groups, carbonyl groups, and combinations thereof. In a further preferred embodiment, the reactive group is an amino group.

Aminated polymeric materials useful in practicing the present invention can be readily produced through a number of methods well known in the art. For example, amines may be introduced into a preformed polymer by plasma treatment of materials with ammonia gas as found in Holmes and Schwartz, *Composites Science and Technology*, 38: 1–21 (1990). Alternatively, amines can be provided by grafting acrylamide to the polymer followed by chemical modification to introduce amine moieties by methods well known to those skilled in the art, e.g., Hofmann rearrangement reaction. A grafted acrylamide-containing polymer may be prepared by radiation grafting as set forth in U.S. Pat. No. 3,826,678 to Hoffman et al. A grafted N-(3-aminopropyl) methacrylamide-containing polymer may be prepared by ceric ion grafting as set forth in U.S. Pat. No. 5,344,455 to Keogh et al., which issued on Sep. 6, 1994. Polyvinylamines or polyalkylimines can also be covalently attached to polyurethane surfaces according to the method taught by U.S. Pat. No. 4,521,564 to Solomone et al., which issued on Jun. 5, 1984. Alternatively, for example, aminosilane may be attached to the surface as set forth in U.S. Pat. No. 5,053,048 to Pinchuk, which issued on Oct. 1, 1991.

In an exemplary embodiment, a polymeric coating material, or a precursor material is exposed to a high frequency plasma with microwaves or, alternatively, to a high frequency plasma combined with magnetic field support to yield the desired reactive surfaces bearing at least a substantial portion of reactant amino groups upon the substrate to be derivatized with the bioactive material.

A functionalized coating surface can also be prepared by, for example, first submitting a coating component to a chemical oxidation step. This chemical oxidation step is then followed, for example, by exposing the oxidized substrate to one or more plasma gases containing ammonia and/or organic amine(s) which react with the treated surface.

In a preferred embodiment, the gas is selected from the group consisting of ammonia, organic amines, nitrous oxide, nitrogen, and combinations thereof. The nitrogen-containing moieties derived from this gas are preferably selected from amino groups, amido groups, urethane groups, urea groups, and combinations thereof, more preferably primary amino groups, secondary amino groups, and combinations thereof.

In another preferred embodiment, the nitrogen source is an organic amine. Examples of suitable organic amines include, but are not limited to, methylamine, dimethylamine, ethylamine, diethylamine, ethylmethylamine, n-propylamine, allylamine, isopropylamine, n-butylamine, n-butylmethylamine, n-amylamine, n-hexylamine, 2-ethylhexylamine, ethylenediamine, 1,4-butanediamine, 1,6-hexanediamine, cyclohexylamine, n-methylcyclohexylamine, ethyleneimine, and the like.

In further preferred embodiment, the chemical oxidation step is supplemented with, or replaced by, submitting the polymer to one or more exposures to plasma-gas that contains oxygen. In yet a further preferred embodiment, the oxygen-containing plasma gas further contains argon (Ar) gas to generate free radicals. Immediately after a first-step plasma treatment with oxygen-containing gases, or oxygen/argon plasma gas combinations, the oxidized polymer is preferably functionalized with amine groups. As mentioned above, functionalization with amines can be performed with plasma gases such as ammonia, volatile organic amines, or mixtures thereof.

In an exemplary embodiment utilizing ammonia and/or organic amines, or mixtures thereof, as the plasma gases, a frequency in the radio frequency (RF) range of from about 13.0 MHz to about 14.0 MHz is used. A generating power of from 0.1 Watts per square centimeter to about 0.5 Watts per square centimeter of surface area of the electrodes of the plasma apparatus is preferably utilized. An exemplary plasma treatment includes evacuating the plasma reaction chamber to a desired base pressure of from about 10 to about 50 mTorr. After the chamber is stabilized to a desired working pressure, ammonia and/or organic amine gases are introduced into the chamber. Preferred flow rates are typically from about 200 to about 650 standard mL per minute. Typical gas pressure ranges from about 0.01 to about 0.5 Torr, and preferably from about 0.2 to about 0.4 Torr. A current having the desired frequency and level of power is supplied by means of electrodes from a suitable external power source. Power output is up to about 500 Watts, preferably from about 100 to about 400 Watts. The plasma treatment can be performed by means of a continuous or batch process.

In the case of batch plasma treatment, a preferred plasma surface treatment system is the PLASMA SCIENCE PS 0350 (HIMONT/PLASMA SCIENCE, Foster City, Calif.)

Optimization procedures for the plasma treatment and the effect of these procedures on the characteristics and the performance of the reactive polymers can be determined by, for example, evaluating the extent of substrate functionalization. Methods for characterizing functionalized polymers are well known in the art.

The result of the above-described exemplary methods is preferably a polymeric surface, which contains a significant number of primary and/or secondary amino groups. These groups are preferably readily reactive at room temperature with an inherent, or an appended, reactive functional group on the bioactive material.

Once the amine-containing polymeric coating is prepared, it can be used to covalently bind biologically active molecules having a variety of functional groups including, for example, ketones, aldehydes, activated carboxyl groups (e.g. activated esters), alkyl halides and the like.

Synthesis of specific biologically active material-polymer conjugates is generally accomplished by: 1) providing a coating component comprising an activated polymer, such as an acrylic acid, and a biologically active agent having a position thereon which will allow a linkage to form; 2) reacting the complementary substituents of the biologically active agent and the coating component in an inert solvent, such as methylene chloride, chloroform or DMF, in the presence of a coupling reagent, such as 1,3-diisopropylcarbodiimide or any suitable dialkyl carbodiimide (Sigma Chemical), and a base, such as dimethylaminopyridine, diisopropyl ethylamine, pyridine, triethylamine, etc. Alternative specific syntheses are readily accessible to those of skill in the art (see, for example, Greenwald et al., U.S. Pat. No. 5,880,131, issued Mar. 9, 1999.

By way of example, the discussion below is concerned with the attachment of a peptide-based bioactive material to an amine-containing polymeric component of a coating of use in practicing the methods of the invention. The choice of a peptide-based biologically active material and an amine-containing polymer is intended to be illustrative of the invention and does not define its scope. It will be apparent to those of skill in the art how to attach a wide range of biologically active agents to polymers comprising amines and other reactive groups.

The conjugates of use in practicing the instant invention, which comprise a peptide, can be synthesized by techniques well known in the medicinal chemistry art. For example, a free amine moiety on a polymeric coating component can be covalently attached to an oligopeptide at the carboxyl terminus such that an amide bond is formed. Similarly, an amide bond may be formed by covalently coupling an amine moiety of an oligopeptide and a carboxyl moiety of a polymeric coating component. For these purposes, a reagent such as 2-(1H-benzotriazol-1-yl)-1,3,3-tetramethyluronium hexafluorophosphate (known as HBTU) and 1-hyroxybenzotriazole hydrate (known as HOBT), dicyclohexylcarbodiimide (DCC), N-ethyl-N-(3-dimethylaminopropyl)-carbodiimide (EDC), diphenylphosphorylazide (DPPA), benzotriazol-1-yl-oxy-tris-(dimethylamino)phosphonium hexafluorophosphate (BOP) and the like, in combination, or singularly, can be utilized.

Furthermore, the instant conjugate can be formed by a non-peptidyl bond between a peptide and a coating component. For example, a peptide can be attached to a coating component through a carboxyl terminus of an oligopeptide via a hydroxyl moiety on a polymeric coating component, thereby forming an ester linkage. For this purpose, a reagent such as a combination of HBTU and HOBT, a combination of BOP and imidazole, a combination of DCC and DMAP, and the like can be utilized.

The instant conjugate can also be formed by attaching the oligopeptide to the polymeric coating component using a linker unit. Such linker units include, for example, a biscarbonyl alkyl diradical whereby an amine moiety on the coating component is connected with the linker unit to form an amide bond and the amino terminus of the oligopeptide is connected with the other end of the linker unit also forming an amide bond. Conversely, a diaminoalkyl diradical linker unit, whereby a carbonyl moiety on the coating component is covalently attached to one of the amines of the linker unit while the other amine of the linker unit is covalently attached to the C-terminus of the oligopeptide, can also be utilized. Other such linker units, which are stable to the physiological environment, are also envisioned.

In addition to linkers that are stable in vivo, linkers that are designed to be cleaved to release the biologically active agent from the polymer are useful in the methods of the present invention. Many such linker arms are accessible to those of skill in the art. Common cleavable linker arms include, for example, specific protease cleavage sequences, disulfides, esters and the like. Many appropriate cleavable cross-linking agents are commercially available from companies, such as Pierce (Rockford, Ill.), or can be prepared by art-recognized methods.

Any of the bioactive agents from the various classes of bioactive agents set forth above can be tethered to a polymer by the methods described herein. In a particularly preferred embodiment, the biologically active material is a taxane. For purposes of the present invention, the term "taxane" includes all compounds within the taxane family of terpenes. Thus, taxol (paclitaxel), 3'-substituted tert-butoxy-carbonyl-amine derivatives (taxoteres) and the like as well as other analogs available from, for example, Sigma Chemical (St. Louis, Mo.) and/or Bristol Meyers Squibb are within the scope of the present invention.

Generally, it is preferred that a taxane having the 2' position available for substitution is reacted with a suitably activated polymer such as a polymeric carboxylic acid under conditions sufficient to cause the formation of a 2' ester linkage between the two substituents.

One skilled in the art understands that in the synthesis of compounds useful in practicing the present invention, one may need to protect various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to PROTECTIVE GROUPS IN ORGANIC CHEMISTRY, McOmie, ed., Plenum Press, NY, N.Y. (1973); and, PROTECTIVE GROUPS IN ORGANIC SYNTHESIS, Greene, ed., John Wiley & Sons, NY (1981) for the teaching of protective groups which may be useful in the preparation of compounds of the present invention.

2. Reversibly Associated Bioactive Materials

Generally, if it is desired that the biologically active agent remain active in the coating for a long period of time, it is preferable to covalently attach the biologically active molecule to the coating itself. In an exemplary embodiment, a bioactive agent is immobilized on a component (e.g., fibrin) of a fibrin sealant. In contrast, if it is desired that the biologically active agent escape the coating (e.g., by diffusion from the coating, erosion of the coating, etc.), the agent should be reversibly associated with the coating. The reversibly associated agent can, for example, be entrapped in a delivery matrix by adding the agent to the matrix components during manufacture of the matrix. In an exemplary embodiment, the agent is added to a polymer melt or a solution of the polymer. Other methods for reversibly incorporating agents into a delivery matrix will be apparent to those of skill in the art.

Examples of such reversible associations include, for example, agents that are mechanically entrapped within the matrix and agents that are encapsulated in structures (e.g., within microspheres, liposomes, etc.) that are themselves entrapped in, or immobilized on, the matrix. Other reversible associations include, but are not limited to, agents that are adventitiously adhered to the coating by, for example, hydrophobic or ionic interactions and agents bound to one or more coating component by means of a linker cleaved by one or more biologically relevant process. The reversibly associated agents can be exposed on the coating surface or they can be covered with the same or a different coating, such as a bioerodable polymer, as described below.

In an exemplary embodiment, the surface character of the coating material is altered or manipulated by including certain additives or modifiers in the coating material during its manufacture. A method of preparing surface-functionalized polymeric materials by this method is set forth in, for example, Caldwell, supra. In the Caldwell method, additives or modifiers are combined with the polymeric material during its manufacture. These additives or modifiers include compounds that have affinity sites, compounds that facilitate the controlled release of agents from the polymeric material into the surrounding environment, catalysts, compounds that promote adhesion between the bioactive materials and the coating material and compounds that alter the surface chemistry of the coating material.

As used herein, the term "affinity site" refers to a site on the polymer that interacts with a complementary site on a biologically active agent, or on the exterior surface of the structure to which the matrix is applied.

Affinity sites contemplated in the practice of the present invention include such functional groups as hydroxyl, carboxyl, carboxylic acid, amine groups, hydrophobic groups, inclusion moieties (e.g., cyclodextrin, complexing agents), biomolecules (e.g. antibodies, haptens, saccharides, peptides) and the like, that promote physical and/or chemical interaction with the bioactive agent or tissue. In the present embodiment, the affinity site interacts with a bioactive agent or tissue by non-covalent means. The particular compound employed as the modifier will depend on the chemical functionality of the biologically active agent and/or the groups on the surface of a particular tissue. Appropriate functional groups for a particular purpose can readily be deduced by one of skill in the art.

In another preferred embodiment, the coating used in the invention is a substantially flowable material that can be delivered to a site of insult by means of, for example, a catheter, needle or other percutaneous delivery device. Preferred embodiments of the substantially flowable material are those that cure to a substantially non-flowable coating in vivo. Materials meeting these criteria include, for example, fibrin sealants, hydrophobic poly(hydroxy acids) and the like. The substantially flowable material will generally include one or more biologically active agents. The amount of a particular biologically active material contained in the substantially flowable material varies depending on a number of factors, including, for example, the activity of the agent and the tenaciousness with which the agent adheres to the delivery matrix. .

In another preferred embodiment, the biologically active material interacts with a surfactant that adheres to the coating material. Presently preferred surfactants are selected from benzalkonium halides and sterylalkonium halides. Other surfactants suitable for use in the present invention are known to those of skill in the art.

In a still further preferred embodiment, the bioactive material interacting with, and adhering to, the coating material is a taxane, a taxane derivative or a combination thereof.

E. Delivery Vehicle Formats

The present invention includes providing a coating layer over a site of insult to an internal structure. In a preferred embodiment, the site of insult is at least partially covered with a coating controlling the release of at least one biologically active material dispersed throughout the coating. Other preferred coatings comprise a reservoir component formed by, or entrapped within, the coating. The reservoir contains the biologically active material and, preferably, controls its release properties. The reservoir can be a monolithic structure or it can be formed by smaller structures dispersed in the coating (e.g., microspheres).

The coating can take a number of forms. For example, useful coatings can be in the form of foams, gels, suspensions, microcapsules, solid polymeric materials and fibrous or porous structures. The coating can be multilayered with one or more of the layers including a biologically active material. Moreover, the coating can be layered on a component impregnated with a biologically active agent. Alternatively, the bioactive agent can be dispersed in one or more components or regions of the coating. Many materials that are appropriate for use as coatings in the present methods are known in the art and both natural and synthetic coatings are useful in practicing the present invention.

1. Selection of Coating Materials

Suitable polymers that can be used as coatings in the present invention include, but are not limited to, water-soluble and water-insoluble, biodegradable and nonbiodegradable polymers. The coatings of use in the present invention are preferably biodegradable, or more preferably bioerodable. The coatings are preferably sufficiently porous, or capable of becoming sufficiently porous, to permit efflux of the biologically active molecules from the coating. The coatings are also preferably sufficiently non-inflammatory and are biocompatible so that inflammatory responses do not prevent the delivery of the biologically active molecules to the tissue. It is advantageous if the coating also provides at least partial protection of the biologically active molecules from the adverse effects of proteases, hydrolases, nucleases and other relevant degradative species. In addition, it is advantageous for the coating to produce controlled, sustained delivery of the biologically active agent.

Many polymers can be utilized to form the coating. A coating can be, for example, a gel, such as a hydrogel, organogel or thermoreversible gel. Other useful polymer types include, but are not limited to, thermoplastics and films. Moreover, the coating can comprise a homopolymer, copolymer or a blend of these polymer types. The coating can also include a drug-loaded microparticle dispersed within a component of the coating, which serves as a dispersant for the microparticles. Microparticles include, for example, microspheres, microcapsules and liposomes.

The coating matrix can serve to immobilize the microparticles at a particular site, enhancing targeted delivery of the encapsulated biologically active molecules. Rapidly bioerodible polymers such as polylactide-co-glycolide, polyanhydrides, and polyorthoesters, whose carboxylic groups are exposed on the surface are useful in the coatings of use in the invention. In addition, polymers containing labile bonds, such as polyesters, are well known for their hydrolytic reactivity. The hydrolytic degradation rates of the coatings can generally be altered by simple changes in the polymer backbone.

The coating can be made up of natural and/or synthetic polymeric materials. Representative natural polymers of use as coatings in the present invention include, but are not limited to, proteins, such as zein, modified zein, casein, gelatin, gluten, serum albumin, or collagen, and polysaccharides, such as cellulose, dextrans, and polyhyaluronic acid. Also of use in practicing the present invention are materials, such as collagen and gelatin, which have been widely used on implantable devices, such as textile grafts (see, for example, Hoffman, et al., U.S. Pat. No. 4,842,575, which issued on Jun. 27, 1989 and U.S. Pat No. 5,034,265, which issued on Jul. 23, 1991), but which have not been utilized as components of adherent coatings for periadventitial delivery of bioactive agents, such as those preventing or retarding the development if intimal hyperpalsia. Hydrogel or sol-gel mixtures of polysaccharides are also known. Furthermore, fibrin, an insoluble protein formed during the blood clotting process, has also been used as a sealant for porous implantable devices (see, for example, Sawhey et al., U.S. Pat. No. 5,900,245, issued May 4, 1999). Useful fibrin sealant compositions are disclosed in, for example, Edwardson et al., U.S. Pat. No. 5,770,194, which issued on Jun. 23, 1998 and U.S. Pat. No. 5,739,288, which issued on Apr. 14, 1998. These and other naturally based agents, alone or in combination, can be used as a coating in practicing the present invention.

Representative synthetic polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly (ethylene glycol), poly(ethylene oxide), poly (ethylene terephthalate), poly(vinyl acetate), polyvinyl chloride, polystyrene, polyvinyl pyrrolidone, pluronics and polyvinylphenol and copolymers thereof.

Synthetically modified natural polymers include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

2. Biodegradable and Bioresorbable Coating Materials

Coating compositions preferably have intrinsic and controllable biodegradability, so that they persist for about a week to about six months. The coatings are also preferably biocompatible, non-toxic, contain no significantly toxic monomers and degrade into non-toxic components. Moreover, preferred coatings are chemically compatible with the substances to be delivered, and tend not to denature the active substance. Still further preferred coatings are, or become, sufficiently porous to allow the incorporation of biologically active molecules and their subsequent liberation from the coating by diffusion, erosion or a combination thereof. The coatings should also remain at the site of application by adherence or by geometric factors, such as by being formed in place or softened and subsequently molded or formed into fabrics, wraps, gauzes, particles (e.g., microparticles), and the like. Types of monomers, macromers, and polymers that can be used are described in more detail below.

Representative biodegradable polymers include, but are not limited to, polylactides, polyglycolides and copolymers thereof, poly(ethylene terephthalate), poly(butyric acid), poly(valeric acid), poly(lactide-co-caprolactone), poly (lactide-co-glycolide), polyanhydrides, polyorthoesters, blends and copolymers thereof. Of particular use are compositions that form gels, such as those including collagen, pluronics and the like.

Still further preferred coatings are water-insoluble materials that comprise within at least a portion of their structure, a bioresorbable molecule. An example of such a coating is one that includes a water-insoluble copolymer, which has a bioresorbable region, a hydrophilic region and a plurality of crosslinkable functional groups per polymer chain.

For purposes of the present invention, "water-insoluble materials" includes copolymers that are substantially insoluble in water or water-containing environments. Thus, although certain regions or segments of the copolymer may be hydrophilic or even water-soluble, the copolymer molecule, as a whole, does not by any substantial measure dissolve in water or water-containing environments.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region is preferably hydrophobic. In another embodiment, however, the bioresorbable region may be designed to be hydrophilic so long as the copolymer composition as a whole is not rendered water-soluble. Thus, the bioresorbable region is designed based on the preference that the copolymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable coatings include, for example, synthetically produced resorbable block copolymers of poly(α-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J. Biomed. Mater. Res.* 21: 1301–1316 (1987); and Cohn et al., *J. Biomed. Mater. Res.* 22: 993–1009 (1988).

Presently preferred bioresorbable polymers include one or more components selected from poly(esters), poly(hydroxy acids), poly(lactones), poly(amides), poly(ester-amides), poly (amino acids), poly(anhydrides), poly(orthoesters), poly(carbonates), poly(phosphazines), poly(phosphoesters), poly(thioesters), polysaccharides and mixtures thereof. More preferably still, the biosresorbable polymer includes a poly(hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used as coatings in the methods of the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other coatings based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a difunctional compound, such as, a diisocyanate, diacylchloride or dichlorosilane.

The monomers, polymers and copolymers of use in the present invention preferably form a stable aqueous emulsion, and more preferably a flowable liquid. The relative proportions or ratios of the bioresorbable and hydrophilic regions, respectively are preferably selected to render the block copolymer composition water-insoluble. Furthermore, these compositions are preferably sufficiently hydrophilic to form a hydrogel in aqueous environments when crosslinked.

The specific ratio of the two regions of the block copolymer composition for use as coatings in the present invention will vary depending upon the intended application and will be affected by the desired physical properties of the implantable coating, the site of implantation, as well as other factors. For example, the composition of the present invention will preferably remain substantially water-insoluble when the ratio of the water-insoluble region to the hydrophilic region is from about 10:1 to about 1:1, on a percent by weight basis.

Preferred bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

As set forth above, the preferred composition also includes a hydrophilic region. Although the present composition contains a hydrophilic region, in preferred coatings, this region is designed and/or selected so that the composition as a whole, remains substantially water-insoluble.

When placed within the body, the hydrophilic region can be processed into excretable and/or metabolizable fragments. Thus, the hydrophilic region can include, for example, polyethers, polyalkylene oxides, polyols, poly (vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly (alkylene) oxide. Such poly(alkylene) oxides can include, for example, poly(ethylene) oxide, poly(propylene) oxide and mixtures and copolymers thereof.

Concerning the disposition of the biologically active agent in the coating, substantially any combination of bioactive compound and coating that is of use in achieving the object of the present invention is contemplated by this invention. In a preferred embodiment, the bioactive material is dispersed in a resorbable coating that imparts controlled release properties to the biologically active agent. The controlled release properties can result from, for example, a resorbable polymer that is cross-linked with a degradable cross-linking agent. Alternatively, the controlled release properties can arise from a resorbable polymer that incorporates the biologically active material in a network of pores formed during the cross-linking process or gelling. In another embodiment, the drug is loaded into microspheres, which are themselves biodegradable and the microspheres are embedded in the coating. Many other appropriate drug/coating formats will be apparent to those of skill in the art.

In another preferred embodiment, an underlying polymeric component of a coating of use in the invention is first impregnated with the biologically active material and a resorbable polymer is layered onto the underlying component. In this embodiment, the impregnated component serves as a reservoir for the bioactive material, which can diffuse out through pores in a resorbable polymer network, through voids in a polymer network created as a resorbable polymer degrades in vivo, or through a layer of a gel-like coating. Other controlled release formats utilizing a polymeric substrate, a bioactive agent and a coating will be apparent to those of skill in the art.

3. Hydrogel-based Coatings

Also contemplated for use in the practice of the present invention as a coating component are hydrogels. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. No. 5,410,016, which issued on Apr. 25, 1995 and U.S. Pat. No. 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly($\alpha$-hydroxy acid), such as polyglycolic acid or polylactic acid. See, Sawhney et al., *Macromolecules* 26: 581–587 (1993).

In a preferred embodiment, the bioactive material is dispersed in a hydrogel that is cross-linked to a degree sufficient to impart controlled release properties to the biologically active agent. The controlled release properties can result from, for example, a hydrogel that is cross-linked with a degradable cross-linking agent. Alternatively, the controlled release properties can arise from a hydrogel that incorporates the biologically active material in a network of pores formed during the cross-linking process.

In another preferred embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another preferred embodiment, a component of the coating is first impregnated with the biologically active material and the hydrogel is layered onto the impregnated coating component. In this embodiment, the impregnated coating component serves as a reservoir for the bioactive material or agent, which can diffuse out through pores in the hydrogel network or, alternatively, can diffuse out through voids in the network created as the hydrogel degrades in vivo (see, for example, Ding et al., U.S. Pat. No. 5,879,697, issued Mar. 9, 1999; and Ding et al., U.S. Pat. No. 5,837,313, issued Nov. 17, 1998). Other controlled release formats utilizing a polymeric substrate, a bioactive agent and a hydrogel will be apparent to those of skill in the art.

As set forth above, useful coatings of the present invention can also include a plurality of crosslinkable functional groups. Any crosslinkable functional group can be incorporated into these compositions so long as it permits or facilitates the formation of a hydrogel. Preferably, the crosslinkable functional groups of the present invention are olefinically unsaturated groups. Suitable olefinically unsaturated functional groups include without limitation, for example, acrylates, methacrylates, butenates, maleates, allyl ethers, allyl thioesters and N-allyl carbamates. Preferably, the crosslinking agent is a free radical initiator, such as for example, 2,2'-azobis (N,N'dimethyleneisobutyramidine) dihydrochloride.

The crosslinkable functional groups can be present at any point along the polymer chain of the present composition so long as their location does not interfere with the intended function thereof. Furthermore, the crosslinkable functional groups can be present in the polymer chain of the present invention in numbers greater than two, so long as the intended function of the present composition is not compromised.

An example of a coating having the above-recited characteristics is found in, for example, Loomis, U.S. Pat. No. 5,854,382, issued Dec. 29, 1998. This coating is exemplary of the types of coatings that can be used in the invention.

Also contemplated by the present invention is the use of coatings that are capable of promoting the release of an agent from the coating. For example, in a preferred embodiment, the bioactive material is dispersed throughout the hydrogel. As the hydrogel degrades by hydrolysis or enzymatic action, the bioactive material is released. Alternatively, the coating may promote the release of a biologically active material by forming pores once the resulting article is placed in a particular environment (e.g., in vivo). In a preferred embodiment, these pores communicate with a reservoir containing the bioactive material. Other such coating components that promote the release of an agent from materials are known to those of skill in the art.

F. Fibrin Sealants

In a particularly preferred embodiment, the drug delivery vehicle used in the methods of the invention is a fibrin sealant. Fibrin sealants having substantially any composition are useful in the methods of the present invention.

Fibrin sealants are biological adhesives whose effect imitates the final stages of coagulation, thereby resulting in a fibrin clot. Conventional fibrin sealants consist of concentrated human fibrinogen, bovine aprotinin and factor XIII, as the first component and bovine thrombin and calcium chloride as the second component. Application is generally carried out with a double-barreled syringe, which permits simultaneous application of both components to the site where one wants to form the fibrin clot. Aprotinin is a fibrinolytic inhibitor, which can be added to promote stability of fibrin sealants.

The fibrinogen component of the fibrin sealant can be prepared from pooled human plasma. The fibrinogen can be concentrated from the human plasma by cryoprecipitation and precipitation using various reagents, e.g., polyethylene glycol, ether, ethanol, ammonium sulfate or glycine. For an excellent review of fibrin sealants, see, Brennan, *Blood Reviews* 5:240–244 (1991); Gibble et al., *Transfusion* 30:741–747 (1990); Matras, *Oral Maxillofac Sura.* 43:605–611 (1985) and Lerner et al., *J. of Surgical Research* 48:165–181 (1990).

Recently, there has also been an interest in the preparation of fibrin sealants that utilize autologous fibrin. An autologous fibrin sealant is a fibrin sealant wherein the fibrinogen component of the fibrin sealant is extracted from the patient's own blood. The use of an autologous fibrin sealant is presently preferred because it eliminates the risk of transmission of blood-transmitted infections, e.g., hepatitis B, non A, non B hepatitis and acquired immune deficiency syndrome (AIDS), that could otherwise be present in the fibrinogen component extracted from pooled human plasma. See, Silberstein et al., *Transfusion* 28:319–321 (1988); Laitakari et al., *Laryngoscope* 99:974–976 (1989) and Dresdale et al., *Ann. Thoracic Surgery* 40:385–387 (1985).

Fibrin sealants useful in the methods of the invention can utilize crosslinked fibrin sealants, non-cross-linked fibrin sealants and combinations thereof. Non-limiting examples of non-crosslinked fibrin are non-crosslinked fibrin I, non-crosslinked fibrin II and des BB fibrin, with non-crosslinked fibrin I being preferred. Mixtures of non-crosslinked fibrin can be present. Also, for the purpose of the subject invention "crosslinked fibrin" includes any form of fibrin resulting from the conversion of non-crosslinked fibrin to crosslinked fibrin. Thus, the crosslinked fibrin, for example, resulting from the conversion of non-crosslinked fibrin I to crosslinked fibrin, can be crosslinked fibrin I and/or crosslinked fibrin II, depending on how the conversion step is carried out.

F. Microencapsulation of Bioactive Material

In another preferred embodiment, the biologically active material is incorporated into a polymeric component by encapsulation in a microcapsule. The microcapsule is preferably fabricated from a material different from that of the bulk of the coating matrix.

Preferred microcapsules are those which are fabricated from a material that undergoes erosion in the host, or those which are fabricated such that they allow the bioactive agent to diffuse out of the microcapsule. Such microcapsules can be used to provide for the controlled release of the encapsulated biologically active material from the microcapsules.

Numerous methods are known for preparing microparticles of any particular size range. In the various delivery vehicles of the present invention, the microparticle sizes may range from about 0.2 micron up to about 100 microns. Synthetic methods for gel microparticles, or for microparticles from molten materials, are known, and include polymerization in emulsion, in sprayed drops, and in separated phases. For solid materials or preformed gels, known methods include wet or dry milling or grinding, pulverization, size separation by air jet, sieve, and the like.

Microparticles can be fabricated from different polymers using a variety of different methods known to those skilled in the art. Exemplary methods include those set forth below detailing the preparation of polylactic acid and other microparticles.

Polylactic acid microparticles are preferably fabricated using one of three methods: solvent evaporation, as described by Mathiowitz, et al., *J. Scanning Microscopy* 4:329 (1990); Beck, et al., *Fertil. Steril.* 31: 545 (1979); and Benita, et al., *J. Pharm. Sci.* 73: 1721 (1984); hot-melt microencapsulation, as described by Mathiowitz, et al., *Reactive Polymers* 6: 275 (1987); and spray drying. Exemplary methods for preparing microencapsulated bioactive materials useful in practicing the present invention are set forth below.

1. Solvent Evaporation

In this method, the microcapsule polymer is dissolved in a volatile organic solvent, such as methylene chloride. The drug (either soluble or dispersed as fine particles) is added to the solution, and the mixture is suspended in an aqueous solution that contains a surface active agent such as poly (vinyl alcohol). The resulting emulsion is stirred until most of the organic solvent has evaporated, leaving solid microparticles. The solution is loaded with a drug and suspended in vigorously stirred distilled water containing poly(vinyl alcohol) (Sigma). After a period of stirring, the organic solvent evaporates from the polymer, and the resulting microparticles are washed with water and dried overnight in a lyophilizer. Microparticles with different sizes (1–1000 microns) and morphologies can be obtained by this method. This method is useful for relatively stable polymers like polyesters and polystyrene. Labile polymers such as polyanhydrides, may degrade during the fabrication process due to the presence of water. For these polymers, the following two methods, which are performed in completely anhydrous organic solvents, are preferably used.

2. Hot Melt Microencapsulation

In this method, the polymer is first melted and then mixed with the solid particles of biologically active material that have preferably been sieved to less than 50 microns. The mixture is suspended in a non-miscible solvent (like silicon oil) and, with continuous stirring, heated to about 5° C. above the melting point of the polymer. Once the emulsion is stabilized, it is cooled until the polymer particles solidify. The resulting microparticles are washed by decantation with a solvent such as petroleum ether to give a free-flowing powder. Microparticles with sizes ranging from about 1 to about 1000 microns are obtained with this method. The external surfaces of capsules prepared with this technique are usually smooth and dense. This procedure is preferably used to prepare microparticles made of polyesters and polyanhydrides.

3. Solvent Removal

This technique is preferred for polyanhydrides. In this method, the biologically active material is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. Microparticles that range from about 1 to about 300 microns can be obtained by this procedure. The external morphology of spheres produced with this technique is highly dependent on the type of polymer used.

4. Spray-Drying

In this method, the polymer is dissolved in methylene chloride. A known amount of the active drug is suspended (insoluble drugs) or co-dissolved (soluble drugs) in the polymer solution. The solution or the dispersion is then spray-dried. Microparticles ranging between about 1 to about 10 microns are obtained with a morphology which depends on the type of polymer used.

5. Hydrogel Microparticles

In a preferred embodiment, the bioactive material is encapsulated in microcapsules that comprise a sodium alginate envelope.

Microparticles made of gel-type polymers, such as alginate, are preferably produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100–170 RPM) ionic hardening bath is positioned below the extruding device to catch the forming microdroplets. The microparticles are left to incubate in the bath for about twenty to thirty minutes in order to allow sufficient time for gelation to occur. Microparticle size is controlled by using various size extruders or varying either the nitrogen gas or polymer solution flow rates.

6. Liposomes

Liposomes are commercially available from a variety of suppliers. Alternatively, liposomes can be prepared according to methods known to those skilled in the art, for example, as described in Eppstein et al., U.S. Pat. No. 4,522,811, which issued on Jun. 11, 1985. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, are of use in the present invention.

G. Bioactive Agent Release Rates

In another preferred embodiment, the methods of the invention include the use of two or more populations of bioactive agents. The populations are distinguished by, for example, having different rates of release from the coating of the invention. Two or more different rates of release can be obtained by, for example, incorporating one agent population into the bulk coating and the other agent population into microcapsules embedded in the bulk coating. In another exemplary embodiment, the two agents are encapsulated in microspheres having distinct release properties. For example, the first agent is encapsulated in a liposome and the second agent is encapsulated in an alginate microsphere.

Other characteristics of the populations in addition to their release rates can be varied as well. For example, the two populations can consist of the same, or different agents. Moreover, the concentrations of the two populations can differ from each other. For example, in certain applications it is desirable to have one agent released rapidly (e.g., an antibiotic) at a first concentration, while a second agent is released more slowly at a second concentration (e.g., an inhibitor of tissue overgrowth). Furthermore when two or more distinct agents are used they can be distributed at two or more unique sites within the delivery vehicle.

In yet a further embodiment, the delivery vehicle of the invention can control the release of two or more agents acting in concert to achieve a biological effect. For example, vascular endothelial growth factor (VEGF)can initially be released from the matrix to recruit new vessels to a tissue. Some time prior to or after the exhaustion of the VEGF, a second agent, such as fibroblast growth factor (Fgf) is released to stabilize the newly recruited vessels. Many other such permutations of agent types, agent concentrations and agent release rates will be readily apparent to those of skill in the art.

H. Formation of a Polymer Matrix

In a preferred embodiment, a solid, flexible drug delivery vehicle matrix is formed by dispensing a flowable polymer, or polymer precursor, formulation onto the surface of a tissue which is surrounded by an aqueous medium. The formulation can be applied to a patient's tissues by any convenient technique. For example, the formulation can be applied by brushing, spraying, extruding, dripping, injecting, or painting. Spraying, via aerosolization is a preferred method of administration because it minimizes the amount of formulation applied to the site of insult while maximizing uniformity. A thin, substantially uniform matrix, such as that formed by spraying, can also be called a film. Typically, the film has a thickness of about 10 $\mu$m to about 10 mm, more preferably from about 20 $\mu$m to about 5 mm. Spraying is a preferred method for applying the polymer formulation to a large surface area, such as peritoneal sidewalls. In contrast, dripping may be preferred for applying the polymer formulation to a small surface area, such as a bowel resection or an anastomosis derived from a coronary artery bypass.

I. Characterization

Characterization of the bioactive agent, the coatings and the combination of the bioactive agent and the coating can be performed at different loadings of bioactive material to investigate coating and encapsulation properties and morphological characteristics of the coatings and microparticles. Microparticle size can be measured by quasi-elastic light scattering (QELS), size-exclusion chromatography (SEC) and the like. Drug loading can be measured by dissolving the coating or the microparticles into an appropriate solvent and assaying the amount of biologically active molecules using one or more art-recognized techniques. Useful techniques include, for example, spectroscopy (e.g., IR, NMR, UV/Vis, fluorescence, etc.), mass spectrometry, elemental analysis, HPLC, HPLC coupled with one or more spectroscopic modalities, and other appropriate means.

J. Kits

The present invention also provides kits comprising the drug delivery vehicles of the invention. By way of example, a fibrin sealant kit is described herein. The focus on fibrin sealant is intended to be illustrative and does not limit the scope of the invention.

The kit can contain as a first component a composition comprising fibrin monomer and a buffer that is capable of solubilizing the fibrin monomer or distilled water, depending on how the solubilization step was performed. The second component can optionally contain a source of calcium ions and/or thrombin. Alternatively, the first component can be a composition comprising noncrosslinked fibrin and the second component can be a source of calcium ions. If the source of fibrinogen utilized to prepare a composition comprising noncrosslinked fibrin is from cell cultures that secrete fibrinogen or recombinant fibrinogen, the first component can be a composition comprising noncrosslinked fibrin, the second component can be a source of calcium ions and a third component is activated factor XIII.

In another embodiment, the kit comprises one or more antihyperplastic agents, thrombin and a source of calcium ions. In this embodiment, the fibrin is preferably derived from plasma removed from the patient into whom the delivery vehicle of the invention will be implanted.

In addition to the drug delivery vehicle of the invention, the kit also contains directions concerning the use of the delivery vehicles for coating a site of insult on an external surface of an internal structure. The kits can also optionally contain a device for administering the vehicle in the method of the invention and biologically active agents to be administered in conjunction with the method of the invention. Other useful kit configurations will be apparent to those of skill in the art.

K. Methods of Treating Intimal Hyperplasia

Patients can be diagnosed for intimal hyperplasia using known methods, such as X-ray fluoroscopic examination of dye flowing through a particular region of a blood vessel or other visual techniques, the presence of symptoms such as pain, based on clinical judgment, or signs evidenced physical examination. Alternatively, it can be assumed that hyperplasia will arise due to performance of procedures such as angioplasty, arterial bypass graft, peripheral bypass surgery, or organ transplantation and the patient treated based on the assumption that injury or disease will inevitably arise.

In one embodiment, a coating comprising a bioactive agent is applied to the site of insult during an open-field procedure. In another embodiment, the coating-drug composite are placed at the site of insult via percutaneous means.

If intimal hyperplasia had been observed prior to implanting or wrapping the strips of matrices, the regression of hyperplasia is typically evidenced by a decrease in pain or other symptoms of decreased blood flow, or through the use of imaging techniques. The decrease in hyperplasia or increase in flow rate through the injured vessel can be monitored by the same methods used to initially diagnose the injury to the vascular endothelium or blockage of the blood vessel.

EXAMPLES

1.1 Materials

Paclitaxel® was obtained from Angiotech Pharmaceuticals, Inc. (Vancouver, Canada), and was supplied in proprietary micellar or delayed-release microsphere formulations.

Fibrin Sealant, was supplied as Tisseel Fibrin Sealant kits, which were purchased from Baxter Healthcare Corp. These kits contained fibrinogen prepared from human plasma, and human thrombin.

Human FXIII was purchased from Enzyme Research Labs, So. Bend Ind., and filter sterilized prior to use.

Reagents for all solutions were Reagent grade or better.

1.2 Methods

1.2a Method of Test Article and Vehicle Preparation

The fibrin polymer formulation, polymerized from a mixture containing a final concentration of 25–30 mg/ml fibrinogen, 5 IU human factor XIII, 50 IU human thrombin, ±Paclitaxel® was prepared by the following method. 157 IU hFXIII was resuspended in 4 ml saline, mixed gently and sterilized by filtration and held until use on ice. The resulting solution (2 ml) was added to each of two vials of the Sealer Protein Concentrate (human) component of the Tisseel kit containing approximately 190 mg fibrinogen/vial. The reconstituted sealant vials were inverted to wet the pellet, and the vials held at 37° C. for 10 minutes. An additional 2 ml of saline (±Paclitaxel®) was introduced into each vial, with continued gentle stirring. After visual inspection to insure reconstitution of the Sealer Protein Concentrate, the contents of the vials were pooled and held at ambient temperature until use within 2 hours. Formation of the fibrin polymer network was initiated at the vivarium by combination with a solution of human thrombin (100 IU/mL) in 20 mM $CaCl_2$. The polymer was applied using the mixing devices supplied with the Tisseel kit.

Micellar Paclitaxel® was prepared as described as follows. Briefly, 4 mL sterile saline was added to one vial of Paclitaxel® reagent (11 mg/vial) and the vial incubated at 55° C. for 5 minutes. The vial was mixed by vigorous vortexing for at least 2 minutes. The clear solution (2 mL) was added to the Sealant Protein Concentrate as described above.

Paclitaxel® microsphere solutions were prepared as follows. Each vial of Paclitaxel® formulated in delayed-release microspheres was reconstituted with 4 mL sterile saline, and 2 ml of this mixture was added per vial of Sealant Protein Concentrate.

1.2b Animal Procedures

Dogs were purchased from Covance, a USDA approved vendor (10 male and 2 female young adult animals) and quarantined as described in QCOP B600. Animals received standard laboratory diet proscribed in QCOP B618, with supplements provided at the discretion of a veterinarian; water was available ad libitum.

Preoperative status of the animals was assessed by obtaining a baseline blood analysis including complete blood count and serum chemistries (IDEXX Veterinary Services, Inc. West Sacramento, Calif.) and by physical evaluation of the animals to monitor weight, body temperature, heart and respiratory rates. The animals were prepared for surgery by insertion of an intravenous (iv) catheter placed in the cephalic vein.

Anesthesia was introduced through the cephalic iv catheter as described in QCOP B803. An endotracheal tube was placed, and respiratory support provided. Anesthesia was maintained using a mixture of isoflurane in oxygen. Lactated Ringers supplemented with a prophylactic admixture of antibiotic (Cefazolin) was supplied intravenously.

Using aseptic surgical techniques, the femoral arteries and veins were exposed and isolated. The veins were ligated and the proximal end tagged, and a segment harvested. The isolated vessel was flushed with saline and trimmed to the desired size. A bilateral exposure of the carotid arteries was performed.

The animal was heparinized (100 IU/ kg body weight), and anticoagulated at the surgeon's discretion with additional heparin. The carotid artery was cross-clamped and transected. An interpositional graft with end-to-side anastamoses of the femoral vein to the carotid artery was performed. Anastomoses were identified with a surgical staple. Where indicated, the test or control articles were applied to a uniform thickness and allowed to harden. Grafts were placed in both carotid arteries, with the procedures done in series.

Balloon injury to the femoral arteries by three sequences of inflation and removal of a 4 Fr. Fogarty catheter generated 5 cm lesions in each femoral artery that were or were not treated with test/control articles. Injured areas were tagged with a staple. The insertion site was repaired and the animal was closed.

Post-operative care was performed as described in QCOP B809, along with prophylactic administration of antibiotics (Sulfamethoxaxole and Trimethoprin); analgesics were supplied as described in QCOP B803. 7 days post surgery, animals received 250 mg/day aspirin. The wound site was debrided and temperature, heart rate and respiratory rates were monitored daily the week following surgery. Angiography of the carotid sites was performed following surgery and monthly thereafter. Intravascular ultrasound (IVUS) was used to examine the vein grafts in 10 animals at the 12 week endpoint of the study.

At the termination of the experiment, the overall health of the animals was monitored, including routine blood work. Animals were anti-coagulated with heparin (300 IU/kg body weight) and angiography and IVUS measurements of treated vessels were taken. Animals were anesthetized and euthanized as described in QCOP B803 and B621 respectively.

Carotid arteries were exposed and the healing response was evaluated. The grafts, including anastomoses, were fixed under pressure in situ, and were removed along with 4 cm of proximal and distal host vessel. Femoral arteries were exposed and the healing response was observed. The femoral arteries were then fixed under pressure and removed with distal and proximal host tissue. Femoral and carotid arteries were stored in 10% neutral-buffered formalin until analysis by histology. Specimens for histological evaluation were processed and stained with Hematoxalin and Eosin and with Mallory's Trichrome by IDEXX Veterinary Services, West Sacramento, Calif.

1.2c Data Analysis

1.2c1 Carotid Vein Grafts

Image analysis was performed by a qualified vascular surgeon who also analyzed the data. REF Images from angiography were captured on a VHS tape. Digital images were captured from this tape and saved after which they were evaluated using NIH Image. The lumenal width of the native arterial segments proximal and distal to the vein grafts, and the proximal and distal anastomoses were measured. The percent stenoses of the anastomoses relative to the adjacent native arterial segment were reported.

1.2c1a Femoral Arteries

Angiography of the femoral arteries was performed at the termination of the experiment. Images were captured as described above and analyzed using NIH Image. Injured areas were identified by radio-opaque clips, and by anatomy.

The lumenal widths of the arterial segments were measured just distal to the arteriotomy, and in the mid- and distal portions of the injured segments. The percent stenoses of the anastomoses relative to the adjacent native arterial segment were reported. The mean and least values were reported.

Histology of the femoral arteries was analyzed with Adobe Photoshop. Briefly, (1) the lumen-vessel interface, (2) the internal elastic lamina, and (3) the external elastic lamina were traced on digital images from H&E stained tissue with the greatest amount of hyperplasia. The intimal area was determined by subtracting the area encompassing (2) from (1). The medial area was determined by subtracting the area encompassing (2) from (3). The area was measured as (1).

1.3 Results
1.3a Animal Studies
1.3a1 Clinical Observations

The animals were assigned to test groups as shown in Table 1. All dogs recovered uneventfully from surgery and anesthesia. In control animals, subcutaneous hematomas that resolved with time were observed in the carotid (1/3) and femoral sites (1/3). Subcutaneous hematomas at the carotid site were also observed in animals treated with the vehicle (2/3) or vehicle+Paclitaxel® (4/8); these lesions resolved with time. 2/8 animals treated with Paclitaxel® had a hematoma at the femoral site, which also reduced in sized with time and healed well. Except where noted, all incision sites remained dry.

Two animals were sacrificed prior to the termination of the experiment. Animal 12 had uncontrolled bleeding from the left femoral site 13 d post-surgery which was ligated and repaired. 28–30 d post- surgery, bleeding from the right carotid site in animal 12 that could not be managed by discontinuing aspirin and pressure led to early termination of this animal. Animal 11 was observed with a large swelling at the left carotid area and altered mental status 8 weeks post-surgery and was euthanized and explanted. Interestingly, both animals were treated with the delayed release formulation of Paclitaxel®.

1.3b1 Angiography and IVUS

The stenosis and blood flow through grafts was assessed using angiography. Angiography showed that all carotid grafts were patent at the conclusion of surgery, and that the carotid grafts of the surviving animals were patent at the termination of the study (12 weeks). Angiography at the termination of the experiment showed that both femoral arteries in 8/10 animals were patent; one femoral artery in Animal 6 and Animal 10 appeared to be occluded at 12 weeks.

IVUS was used to evaluated carotid grafts in 10 animals at the 12 week time point. Images showed patent vessels, with some suggestion of intimal thickening in some samples. The images were not evaluated further.

1.3c Quantitative Analysis of Angiography and Histology
1.3c1 Carotid Vein Grafts Images were captured as described in section above, and were evaluated by NIH Image. The lumenal width of native arterial segments proximal and distal to the graft and the proximal and distal anastomoses were measured. The per cent stenoses of the anastomoses relative to the native artery are reported in Table 2. There was one animal in the Fibrin Sealant+microsphere Paclitaxel® due to mortality of two of the animals; all other treatment groups represent data from three animals. The per cent stenoses of carotid grafts in animals treated with Paclitaxel® compared with untreated animals is shown in Table 3.

TABLE 2

% Stenoses of Carotid Grafts as Assessed by Angiography

| Treatment | Number of Dogs | Number of Vessels Evaluated | Proximal Anastomotic Site (mean ± s.d) | Distal Anastomotic Site (mean ± s.d.) |
|---|---|---|---|---|
| No. Treatment, Control | 3 | 6 | 28.4 ± 14% | 9.9 ± 13.4% |
| Fibrin vehicle | 3 | 6 | 7.0 ± 8.0%* | 6.9 ± 9.5% |
| Fibrin vehicle ± micellar Paclitaxel ® | 3 | 6 | 7.9 ± 6.4%* | 7.9 ± 6.4%* |
| Fibrin vehicle ± microsphere Paclitaxel ® | 1 | 2 | 0.0 ± 0.0%* | 0% |

*P < 0.05 vs. Control; Anova

TABLE 3

Per Cent Stenoses of Carotid Grafts ± Paclitaxel ® as Assessed by Angiography

| Treatment: Paclitaxel ® | Number of Dogs | Number of Vessels Evaluated | Proximal Anastomotic Site (mean ± s.d) | Distal Anastomotic Site (mean ± s.d.) |
|---|---|---|---|---|
| No | 6 | 12 | 15.9 ± 14.3% | 8.4 ± 11.2% |
| Yes | 4 | 8 | 5.9 ± 6.5%* | 1.1 ± 2.2%** |

*P = 0.08, yes vs. no.
**P = 0.09 yes vs. no.
The histology of tissue sections, although not quantitatively evaluated, correlated with the estimation of hyperplasia by angiography. (data not shown) REF 1.3c2 Balloon—injured Femoral Arteries: Angiography and Histology Images from angiography were captured and analyzed as described previously. The lumenal widths of the arterial segments were measured immediately distal to the arteriotomy, and in the mid- and distal portions of the injured segments. The data are expressed as a ratio of the measurement of injured : uninjured regions of the vessel and are reported in Tables 4 and 5. No significant differences were detected between treatment groups using angiography to measure lumenal width.

TABLE 4

Lumen Width of Balloon-Injured Segments Relative to Native Vessel Assessed by Angiography.

| Treatment: Paclitaxel ® | Number of Dogs | Number of Vessels Evaluated | Mean Lumenal Width (mm) (Mean ± s.d.) | Least Lumenal Width (mm) (Mean ± s.d) |
|---|---|---|---|---|
| No Treatment, Control | 3 | 6 | 1.54 ± 0.18 | 1.23 ± 0.63 |
| Fibrin vehicle | 3 | 6 | 1.50 ± 0.3 | 1.41 ± 0.27 |
| Fibrin vehicle ± micellar Paclitaxel ® | 3 | 6 | 1.40 ± 0.25 | 1.32 ± 0.28 |
| Fibrin vehicle ± microsphere Paclitaxel ® | 1 | 2 | 1.63 ± 0.09 | 1.55 ± 0.12 |

TABLE 5

Lumen Width of Balloon-Injured Segments Relative to Native Vessel ± Paclitaxel®

| Treatment: Paclitaxel® | Number of Dogs | Number of Vessels Evaluated | Mean Lumenal Width (mm) (Mean ± s.d.) | Least Lumenal Width (mm) (Mean ± s.d) |
|---|---|---|---|---|
| No | 6 | 12 | 1.46 ± 0.24 | 1.37 ± 0.27 |
| Yes | 4 | 8 | 1.52 ± 0.24 | 1.32 ± 0.47 |

Histology of sections from areas spanning proximal and distal regions of the balloon-injured femorals and of native tissue proximal to the arteriotomy were evaluated by morphometric analysis as described above. Measures of the lumen, intima, and media from areas with the greatest hyperplasia are shown in Table 6, and this data was analyzed with regard to presence or absence of Paclitaxel® and is presented in Table 7 and 8, respectively.

TABLE 7

Measurement (Area) of Components of Femoral Artery in Regions of Intimal Hyperplasia

| Treatment | Number of Dogs | Number of Vessels Evaluated | Media (mm$^2$) (Mean ± s.d.) | Intima (mm$^2$) (Mean ± s.d.) | Intima: Media Ratio | Lumen (mm$^2$) (Mean ± s.d) |
|---|---|---|---|---|---|---|
| No Treatment | 3 | 6 | 2.31 ± 0.50 | 0.92 ± 0.68 | 0.43 ± 0.37 | 3.09 ± 1.58 |
| Fibrin vehicle | 3 | 6 | 3.29 ± 0.73* | 2.34 ± 1.20* | 0.7 ± 0.28 | 3.82 ± 1.02 |
| Fibrin vehicle ± micellar Paclitaxel® | 3 | 6 | 3.59 ± 0.87* | 2.29 ± 0.86* | 0.63 ± 0.17 | 4.91 ± 1.21* |
| Fibrin vehicle ± microsphere Paclitaxel® | 1 | 2 | 2.75 ± 0.34 | 0.96 ± 0.86 | 0.37 ± 0.36 | 5.19 ± 0.57** |

*P < 0.05, treatment vs. control
**P = 0.06 Fibrin vs. Fibrin + Micellar Paclitaxel®

TABLE 8

Measurement (Area) of Femoral Artery in Regions of Intimal Hyperplasia ± Paclitaxel®

| Treatment: Paclitaxel® | Number of Dogs | Number of Vessels Evaluated | Media (mm$^2$) (Mean ± s.d.) | Intima (mm$^2$) (Mean ± s.d.) | Intima: Media Ratio | Lumen (mm$^2$) (Mean ± s.d) |
|---|---|---|---|---|---|---|
| No | 6 | 12 | 2.77 ± 0.77 | 1.63 ± 1.19 | 0.57 ± 0.34 | 3.45 ± 1.32 |
| Yes | 4 | 8 | 3.38 ± 0.84 | 1.95 ± 1.00 | 0.56 ± 0.23 | 4.98 ± 1.05* |

P < 0.05, Treatment vs. Control 1.4 Discussion
1.4a Carotid Grafts

Paclitaxel® limited stenosis at the proximal and distal anastomotic sites (Table 3, P=0.08 and 0.09, respectively), as assessed by angiography at the 12 week endpoint of the experiment. Analysis of the individual treatment groups revealed that the fibrin vehicle, in the absence of paclitaxal, also limited stenosis at anastomotic sites (Table 2). The data in Tale 2 suggest that healing of the vehicle and treatment groups were similar. This interpretation might be due to the small sample size of the study. Consider the example of the vehicle+microsphere Paclitaxel® (slow release formulation) in which the grafts in the surviving animal did not restenose. The trend seen in this example suggests that this formulation may limit stenosis.

1.4b Femoral Arteries

Analysis of the data obtained by angiography suggested there was no significant difference between control, vehicle and Paclitaxel® treatment groups (Table 4 and 5). This contrasts with the data derived by morphometric analysis of histology of the femoral sections with the largest stenotic response. In this case, formulations with Paclitaxel® had a 44% larger lumen width (p</=0.06) in the absence of changes in the intimal: medial ratio (Table 7 and 8). The discrepancy between the data derived by angiography and histology may reflect differences in methodology of measurement, angiography being an in vivo assay with the data measured in one-dimension, while histologic procedures are multi-step, post-mortem procedures quantified in 2 dimensions. These results suggest that histology is the more sensitive assay for this animal model at 12 weeks.

It is understood that the examples and embodiments described herein are for illustrative purposes only and that various modifications or changes in light thereof will be suggested to persons skilled in the art and are to be included within the spirit and purview of this application and are considered within the scope of the appended claims. All publications, patents, and patent applications cited herein are hereby incorporated by reference in their entirety for all purposes.

What is claimed is:

1. A method of preventing or reducing intimal hyperplasia at a site of insult to an internal structure in a subject, said method comprising:

contacting an exterior surface of said internal structure contiguous with said site of insult, with a drug delivery vehicle comprising an intimal hyperplasia preventing agent, wherein said drug delivery vehicle is substantially flowable during application to said exterior surface and substantially adheres to said exterior surface of said internal structure; and said drug delivery vehicle releasing said intimal hyperplasia preventing agent in a time dependent manner, said releasing occurring in an amount effective to prevent or reduce said intimal hyperplasia.

2. The method according to claim 1, wherein said internal structure is a structure having a substantially circular cross-section.

3. The method according to claim 2, wherein said internal structure is a member selected from vascular system component, an intestinal system component, a urinary system component and combinations thereof.

4. The method according to claim 1, wherein said insult is an injury arising from a surgical procedure.

5. The method according to claim 4, wherein said internal structure is a vascular structure and said surgical procedure is a member selected from the group consisting of angioplasty, vascular reconstructive surgery, heart valve replacement, heart transplantation and combinations thereof.

6. The method according to claim 4, wherein said surgical procedure comprises placing a prosthesis at said site of insult on said internal structure.

7. The method according to claim 6, wherein said prosthesis comprises a member selected from a stent, a graft, a valve and combinations thereof at said site of insult on said internal structure.

8. The method according to claim 6, wherein said exterior surface of said vascular structure contacted with said drug delivery vehicle comprises both said prosthesis and said site of insult.

9. The method according to claim 1, wherein said site of insult comprises an anastomosis.

10. The method according to claim 9, wherein said exterior surface of said vascular structure contacted with said drug delivery vehicle comprises said anastomosis.

11. The method according to claim 1, wherein said intimal hyperplasia preventing agent is a member selected from antithrombotics, antiinflammatories, corticosteroids, antimicrotubule agents, antisense oligonucleotides, antineoplaastics, antioxidants, antiplatelets, calcium channel blockers, converting enzyme inhibitors, cytokine inhibitors, growth factors, growth factor inhibitors, growth factor sequestering agents, fibrosis inhibitors, immunosuppressives, tissue factor inhibitor, smooth muscle inhibitors, sulfated proteoglycans, superoxide dismutase mimics, NO, NO precursors and combinations thereof.

12. The method according to claim 11, wherein said antithrombotic is a member selected from heparin, heparin derivatives hirudin, hirudin derivatives and combinations thereof.

13. The method according to claim 11, wherein said corticosteroid is dexamethasone, dexamethasone derivatives and combinations thereof.

14. The method according to claim 11, wherein said antimicrotubule agent is a member selected from taxane, taxane derivatives and combinations thereof.

15. The method according to claim 11, wherein said antiplatelet agent or said fibrosis inhibitor is an inhibitor of collagen synthesis.

16. The method according to claim 15, wherein said inhibitor of collagen synthesis is selected from halofuginore, halofuginore derivatives, $GpII_bIII_a$ and combinations thereof.

17. The method according to claim 1, wherein said drug delivery vehicle is a member selected from bioerodable vehicles, hydrogel vehicles, thermoreversible vehicles, bioresorbable vehicles and combinations thereof.

18. The method according to claim 17, wherein said vehicle comprises a member selected from gels, foams, suspensions, microcapsules, solid polymeric supports and fibrous structures.

19. The method according to claim 17, wherein said vehicle comprises a bioresorbable component.

20. The method according to claim 19, wherein said bioresorbable component is insoluble in water.

21. The method according to claim 20, wherein said bioresorbable component is hydrophobic.

22. The method according to claim 19, wherein said bioresorbable component is hydrolytically and/or enzymatically cleavable.

23. The method according to claim 19, wherein said bioresorbable component is selected from the group consisting of poly(esters), poly(hydroxy acids), poly(lactones), poly(amides), poly(ester-amides), poly (amino acids), poly (anhydrides), poly(orthoesters), poly(carbonates), poly (phosphazines), poly(phosphoesters), poly(thioesters), polysaccharides and mixtures thereof.

24. The method according to claim 23, wherein said bioresorbable component is a poly(hydroxy) acid.

25. The method according to claim 24, wherein said poly(hydroxy) acid comprises a material selected from the group consisting of poly(lactic) acid, poly(glycolic) acid, poly(caproic) acid, poly(butyric) acid, poly(valeric) acid and copolymers and mixtures thereof.

26. The method according to claim 17, wherein said vehicle forms a member selected from excretable fragments, metabolizable fragments and combinations thereof.

27. The method according to claim 18, wherein said gel is a thermoreversible gel.

28. The method according to claim 27, wherein said gel comprises a member selected from pluronics, fibrin sealants, albumin, collagen, gelatin, hydroxypropylmethylcellulose, polyethylene oxide, hyalouronic acid, polysaccharides and combinations thereof.

29. The method according to claim 28, wherein said gel comprises a member selected from polyurethane hydrogel and polyurethane-urea hydrogel.

30. The method according to claim 17, wherein said drug delivery vehicle comprises a member selected from fibrin, fibronectin, thrombin and combinations thereof.

31. A method of preventing or reducing intimal hyperplasia at a site of insult to a vascular structure in a subject, wherein said insult is a member selected from the group consisting of angioplasty, vascular reconstructive surgery and combinations thereof, said method comprising:

contacting an exterior surface of said vascular structure contiguous with said site of insult, with a drug delivery vehicle comprising an intimal hyperplasia preventing agent, wherein said drug delivery vehicle is substantially flowable during application to said exterior surface and substantially adheres to said exterior surface of said internal structure; and said drug delivery vehicle releases said intimal hyperplasia preventing agent in a time dependent manner, said release occurring in an amount effective to prevent or reduce said intimal hyperplasia.

32. The method according to claim 31, wherein said vascular reconstructive surgery comprises placing a member selected from a stent, a graft and combinations thereof at the site of insult.

33. The method according to claim 32, wherein said exterior surface of said vascular structure contacted with said drug delivery vehicle comprises a member selected from both said stent and said site of insult, both said graft and said site of insult and combinations thereof.

34. The method according to claim 31, wherein said site of insult comprises an anastomosis.

35. The method according to claim 34, wherein said exterior surface of said exterior surface of said vascular structure contacted with said drug delivery vehicle comprises said anastomosis.

36. The method according to claim 31, wherein said intimal hyperplasia preventing agent is a member selected from antithrombotics, antiinflammatories, corticosteroids, antimicrotubule agents, antisense oligonucleotides, antineoplaastics, antioxidants, antiplatelets, calcium channel blockers, converting enzyme inhibitors, cytokine inhibitors, growth factors, growth factor inhibitors, growth factor sequestering agents, fibrosis inhibitors, immunosuppressives, tissue factor inhibitor, smooth muscle inhibitors, sulfated proteoglycans, superoxide dismutase mimics, NO, NO precursors and combinations thereof.

37. The method according to claim 36, wherein said antithrombotic is a member selected from heparin, heparin derivatives hirudin, hirudin derivatives and combinations thereof.

38. The method according to claim 36, wherein said corticosteroid is dexamethasone, dexamethasone derivatives and combinations thereof.

39. The method according to claim 36, wherein said antimicrotubule agent is a member selected from taxane, taxane derivatives and combinations thereof.

40. The method according to claim 36, wherein said antiplatelet agent or said fibrosis inhibitor is an inhibitor of collagen synthesis.

41. The method according to claim 40, wherein said inhibitor of collagen synthesis is selected from halofuginore, halofuginore derivatives, $GpII_bIII_a$ and combinations thereof.

42. The method according to claim 31, wherein said drug delivery vehicle is a member selected from bioerodable vehicles, hydrogel vehicles, thermoreversible vehicles, bioresorbable vehicles and combinations thereof.

43. The method according to claim 42, wherein said drug delivery vehicle comprises a member selected from fibrin, fibronectin, thrombin and combinations thereof.

44. A method of treating a disease state of an internal structure in a subject, said method comprising:
 surgically treating said disease state, thereby creating a surgical site; and
 contacting an exterior surface of said internal structure contiguous with said surgical site, with a drug delivery vehicle comprising an intimal hyperplasia preventing agent, wherein said drug delivery vehicle is substantially flowable during application to said exterior surface and substantially adheres to said exterior surface of said internal structure; and
 said drug delivery vehicle releases said intimal hyperplasia preventing agent in a time dependent manner, said release occurring in an amount effective to prevent or reduce said intimal hyperplasia.

45. The method according to claim 44, wherein said internal structure has a substantially circular cross-section.

46. The method according to claim 45, wherein said structure is a member selected from vascular system component, an intestinal system component, a urinary system component and combinations thereof.

47. The method according to claim 44, wherein said internal structure is a vascular structure and said surgical procedure is a member selected from the group consisting of angioplasty, vascular reconstructive surgery and combinations thereof.

48. The method according to claim 47, wherein said vascular reconstructive surgery comprises placing a prosthesis at said surgical site.

49. The method according to claim 48, wherein said prosthesis comprises a member selected from a stent, a graft, a valve and combinations thereof at said site of insult on said internal structure.

50. The method according to claim 48, wherein said exterior surface of said vascular structure contacted with said drug delivery vehicle comprises a member selected from both said stent and said site of insult, both said graft and said site of insult and combinations thereof.

51. The method according to claim 44, wherein said site of insult comprises an anastomosis.

52. The method according to claim 51, wherein said exterior surface of said vascular structure contacted with said drug delivery vehicle comprises said anastomosis.

53. The method according to claim 44, wherein said intimal hyperplasia preventing agent is a member selected from antithrombotics, antiinflammatories, corticosteroids, antimicrotubule agents, antisense oligonucleotides, antineoplaastics, antioxidants, antiplatelets, calcium channel blockers, converting enzyme growth factor sequestering agents, cytokine inhibitors, growth factors, growth factor inhibitors, fibrosis inhibitors, immunosuppressives, tissue factor inhibitor, smooth muscle inhibitors, sulfated proteoglycans, superoxide dismutase mimics, NO, NO precursors and combinations thereof.

54. The method according to claim 53, wherein said antithrombotic is a member selected from heparin, heparin derivatives hirudin, hirudin derivatives and combinations thereof.

55. The method according to claim 53, wherein said corticosteroid is dexamethasone, dexamethasone derivatives and combinations thereof.

56. The method according to claim 53, wherein said antimicrotubule agent is a member selected from taxane, taxane derivatives and combinations thereof.

57. The method according to claim 53, wherein said antiplatelet agent or said fibrosis inhibitor is an inhibitor of collagen synthesis.

58. The method according to claim 57, wherein said inhibitor of collagen synthesis is selected from halofuginore, halofuginore derivatives, $GpII_bIII_a$ and combinations thereof.

59. The method according to claim 44, wherein said drug delivery vehicle is a member selected from bioerodable vehicles, hydrogel vehicles, thermoreversible vehicles, bioresorbable vehicles and combinations thereof.

60. The method according to claim 59, wherein said drug delivery vehicle comprises a member selected from fibrin, fibronectin, thrombin and combinations thereof.

61. The method according to claim 44, wherein said disease is a member selected from peripheral vascular disease, coronary artery disease, cardiac disease, hyperplastic disease.

* * * * *